United States Patent

Waskönig

Patent Number: 5,549,573
Date of Patent: Aug. 27, 1996

[54] SYRINGE

[76] Inventor: Wilhelm Waskönig, Calle Sacramento, 15, 04720 Aguadulce, Spain

[21] Appl. No.: 338,450
[22] PCT Filed: May 18, 1993
[86] PCT No.: PCT/EP93/01237
§ 371 Date: Feb. 15, 1995
§ 102(e) Date: Feb. 15, 1995
[87] PCT Pub. No.: WO93/23097
PCT Pub. Date: Nov. 25, 1993

[30] Foreign Application Priority Data

May 21, 1992 [DE] Germany .............................. 9206878 U
Jun. 13, 1992 [DE] Germany .............................. 42 19 502.0

[51] Int. Cl.⁶ ............................................. A16M 5/00
[52] U.S. Cl. ............................................. 604/218; 604/230
[58] Field of Search ........................... 604/187, 218, 604/219, 222, 228, 230

[56] References Cited

U.S. PATENT DOCUMENTS

| | | | |
|---|---|---|---|
| 812,686 | 2/1906 | Schork et al. | 604/222 |
| 1,154,677 | 9/1915 | Wedig . | |
| 1,687,091 | 10/1928 | Hein | 604/222 |
| 2,578,814 | 12/1951 | Kollsman . | |
| 2,629,376 | 2/1953 | Gallice et al. | 604/222 |
| 2,882,899 | 4/1959 | Nogier et al. | 604/222 |
| 3,581,956 | 6/1971 | Reid | 604/222 |
| 4,266,557 | 5/1981 | Merry | 604/222 |
| 4,515,591 | 5/1985 | Hemmerich et al. | 604/152 |
| 4,632,672 | 12/1986 | Kvitrud . | |

FOREIGN PATENT DOCUMENTS

| | | | |
|---|---|---|---|
| 102070 | 3/1984 | European Pat. Off. . | |
| 1048267 | 12/1953 | France . | |
| 1053583 | 2/1954 | France | 604/222 X |
| 1108413 | 1/1956 | France | 604/222 X |
| 2406988 | 5/1979 | France . | |
| 1566602 | 4/1970 | Germany . | |
| 2024117 | 9/1971 | Germany . | |
| 2451398 | 5/1976 | Germany . | |
| 286277 | 2/1953 | Switzerland | 604/222 X |
| 1179487 | 1/1970 | United Kingdom . | |

*Primary Examiner*—John D. Yasko
*Attorney, Agent, or Firm*—Dennison, Meserole, Pollack & Scheiner

[57] ABSTRACT

A syringe which is suitable for both injection and aspiration includes a plunger movable within a barrel and a gasket disposed at the distal end of the plunger at a narrowed portion of the plunger between two plunger portions of greater diameter. When the plunger is moved, the gasket forms a seal between the inner wall of the barrel and one of the portions of the plunger of greater diameter.

7 Claims, 2 Drawing Sheets

SYRINGE

BACKGROUND OF THE INVENTION

The invention relates to a syringe useful for both injection and aspiration.

Various syringe types are available in which the changes in resistance during movement of the plunger (so-called loss of resistance syringe) is used during localization of the epidural area. Suitable syringes comprising a plastic barrel and plunger have in common that little resistance is off, red to the advance movement of the syringe plunger, so that any change in pressure is directly transmitted and can hence be detected.

In addition, the syringe should have the property that during movement of the plunger the friction between the latter and the inner wall of the barrel is constant over the entire plunger stroke, so that an even plunger movement can be achieved by slight pressure on the plunger itself.

A syringe consisting of plastic and having these properties, intended for once-only use, was developed by Portex. This is a three-part syringe, the main advantage of which lies in the high dimensional accuracy of plunger and barrel, thereby permitting a good pressure transmission with low friction. As a result of the plunger form, however, this syringe could only operate effectively during injection, since during sucking the gasket between the plunger and the inner wall of the barrel only had an inadequate effect, such that when the plunger was retracted the vacuum built up was insufficient to suck in fluid.

A further syringe having the properties as described at the outset has been developed by Braun. However, this syringe revealed the same drawbacks during sucking as the Portex syringe, i.e. use in sucking applications was not generally possible.

A further syringe is described in FR 1,048,267. The gasket shown in FIG. 8 comprises three sections, an innermost of which has a rectangular geometry and extends over the full width of a syringe plunger groove holding the gasket. According to FIG. 7, the gasket can comprise a large outer section of rectangular cross-section pressing against the barrel inner wall of the syringe and a small web-like inner section. The gasket here is fairly rigid and does not provide an adequate sealing effect during injection or sucking.

CH 286 277 describes an injection syringe composed of an outer salient section in a wide-area contact with the inner wall of the barrel of the syringe and of an inner membrane-like section surrounding the syringe plunger.

A gasket for an injection syringe in accordance with FR 1,108,413 comprises an outer section of droplet shape that merges into an inner salient section via a web. Both the outer and the inner sections are in wide-area contact with the barrel inner wall or the plunger of the syringe.

A syringe having an O-ring disposed in an all-round groove of the syringe barrel is known from U.S. Pat. No. 4,632,672.

DE 1,566,602 describes an injection syringe consisting of plastic and having the drawbacks described at the outset.

A flat gasket is used in accordance with DE 2,024,117 for sealing a plunger in relation to a barrel of an injection syringe consisting of plastic.

Further syringes are described in U.S. Pat. No. 1,154,677, U.S. Pat. No. 2,578,814, EP 0,102,070 A2, FR 4 06,988, GB 1,179,487 and DE 2,451,398 A1.

The problem underlying the present invention is to develop a syringe of the type stated at the outset such that it can be used for both injection and sucking, with low friction losses occurring at the same time while the plunger is being moved.

SUMMARY OF THE INVENTION

In order to solve this problem the gasket is composed of an annular outer section creating a sealing effect during injection or sucking and equivalent to a half-O-ring gasket, and of a central flexible skin-like or membrane-like section that is stabilized by the section that is also equivalent to a half-O-ring and that tightly encloses the plunger has the advantage that in the rest position of the plunger a possible rearward movement of the gasket does not take place. The inner section of the gasket is here designed such that resetting forces do not substantially occur, that would otherwise affect the friction forces during movement of the plunger.

The radial extent of the outer section is preferably equal to or greater than that of the inner section, i.e. of the membrane-like section by itself or together with its reinforcement. In a correspondingly preferred form of the gasket, the skin-like or membrane-like sections extending between the salient sections that are in sealing contact with the barrel inner wall or with the plunger should have a radial extent approximately that of the outer section, but at least twice as large as that of the inner section.

The gasket itself or those sections of it interacting with the plunger sections or barrel inner wall are disposed with play between the sections of the plunger when the syringe is not in use, whereas a sealing effect between the barrel inner wall and one of the sections is obtained during injection or sucking.

With the syringe in accordance with the invention, only low friction losses occur between plunger and barrel inner wall, since the plunger is only in minimal contact with the inner wall on account of the gasket. The plunger is always enclosed in substantially straight-line form both when the skin-like or membrane-like section is internal and when this section is limited by the reinforcement designed as a semi-cylindrical ring. A corresponding and substantially linear sealing effect is also obtained between the barrel inner wall and the outer section of the gasket. Accordingly, the force to be exerted to move the plunger is lower than in known syringes, since in the latter a heavier pressure has to be exerted on the side walls to avoid pressure losses.

The fact that the gasket automatically presses against one of the sections, i.e. during injection against the section facing away from the plunger end face and against the plunger inner wall, resulting in an automatic increase in the sealing effect as the pressure increases, ensures high dependability when the syringe is used.

The same considerations apply for sucking, as the increasing vacuum causes an increased sealing effect between the section close to the end face and the barrel inner wall.

A material should be used in the gasket having a density between 2 and 75 Shore, preferably between 30 and 50. This ensures a deformation of the gasket during injection or sucking that causes a greater sealing effect as the pressure effect increases.

The syringe in accordance with the invention is accordingly equally usable for both injection and sucking, with low friction losses thanks to the freely movable arrangement of the gasket with play between the plunger sections or the limits of the receptacle, thereby providing the possibility that the gasket is in sealing contact between one of the plunger sections and the barrel wall depending on whether the syringe is used for injection or for sucking.

Further details, advantages and features of the invention are clear from the following description of an embodiment shown in the drawings.

DESCRIPTION OF THE PREFERRED EMBODIMENTS

Figure 1:
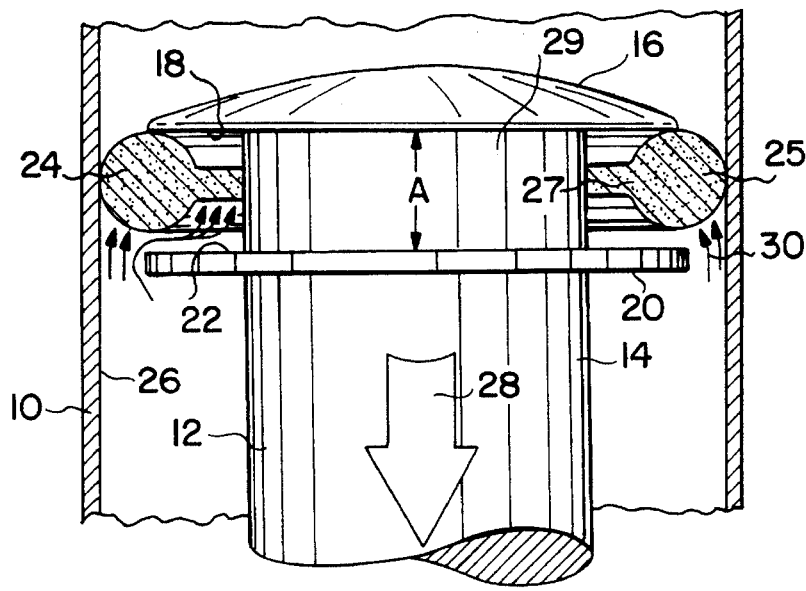
FIG. 1 shows a section through a first embodiment of a syringe during sucking.
Figure 2:
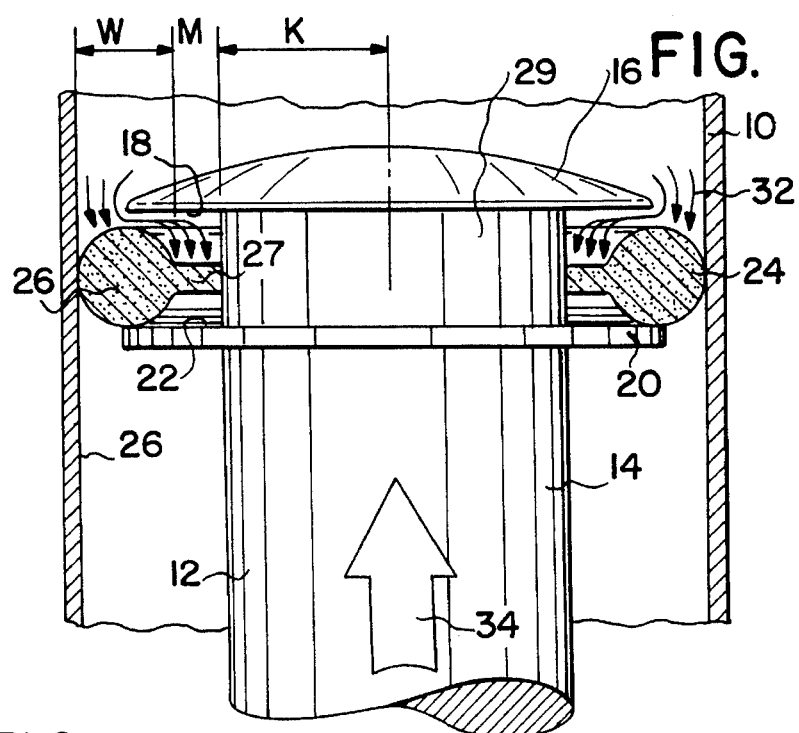
FIG. 2 shows a section through the syringe according to FIG. 1 during injection.

FIGS. 1 and 2 show a section through a disposable syringe preferably made of plastic, using which both injection and sucking is possible. The syringe comprises a hollow barrel (10) with plunger (12) movably disposed therein. The plunger (12) has a cylindrical basic element (14) of which the outer diameter is smaller than the inner diameter of the barrel (10). On the needle side, the plunger (12) has an end section (16) that is curved on the outside and preferably follows the geometry of a spherical section. The end section (16) extends radially beyond the basic element (14) of the plunger (12), however with the maximum outer diameter being smaller than the inner diameter of the barrel (10).

The inner face (18) of the end section (16) extending from the basic element (14) is flat, as indicated in FIGS. 1 and 2.

At a distance from the face (18) is a section (20) of disk shape also extending radially beyond the basic element (14) of the plunger (12), the outer diameter of said section (20) also being less than the inner diameter of the barrel (10). The clear distance between the facing and parallel surfaces (18) and (22) of the end section (16) and of the section (20) respectively is indicated in FIG. 1 with A.

The plunger (12) and the sections (16) and (20) extending therefrom have a diameter that is slightly lower than the inner diameter of the barrel (10), so that direct contact is ruled out.

Disposed between the end section (16) and the section (20), i.e. between the surfaces (18) and (22) is a gasket (24) of which the extent in the axial direction of the plunger (12) is less than the clear distance A. The outer diameter of the gasket (24) is at least equal to the inner diameter of the barrel (10).

The gasket (24) comprises here an outer section (25) of radial extent W equivalent to an O-ring and an inner skin-like of membrane-like section (27) of radial extent M that tightly encloses the plunger section (29) of radius K.

Figure 3:
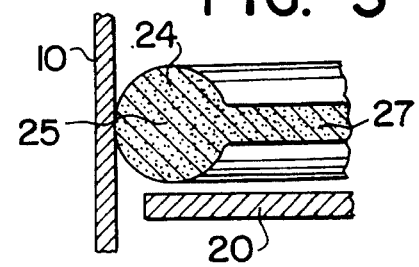
FIG. 3 shows a gasket used in accordance with the invention in a syringe in the rest position.

When a syringe is not in use, the gasket (24) is disposed freely movable with the lowest possible play between the sections (16) and (20). This does not automatically result in sealing between the gasket (24) and one of the sections (16) or (20) and the barrel inner wall (26). This is made clear in FIG. 3.

If the syringe is used for sucking (FIG. 1), the plunger (12) is drawn back from the syringe needle, i.e. in the direction of the arrow (28). This movement compels the gasket (24) to make contact between the surface (18) of the end section (16) and the inner wall (26) of the barrel (10). This results in a sealing effect that increases as the plunger movement intensifies. In the same way, a pressure (indicated by the arrows 30) acts on the gasket (24), thereby increasing the sealing effect.

Consequently, problem-free sucking of fluids is possible. At the same time, however, only low friction resistances have to be overcome, since the toric gasket (24) requires only a small contact area (linear contact) with the barrel wall (26) to become effective. This does not however preclude guide projections extending from the basic element (14) and contacting the inner wall (26).

There is in the same way a linear toric seal between the inner section (27) and the plunger section (29). If necessary, that end of the gasket section (27) pressing against the plunger section can be tapered or chamfered.

Figure 4:
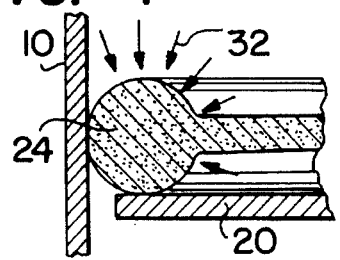
FIG. 4 shows the gasket used in accordance with the invention when the syringe is in use.

However, reliable sealing is obtained with the gasket (24) not only during sucking but also during injection, more precisely between the inner wall (26) and the section (20), as made clear in FIG. 2. Because of the internal pressure buildup in the syringe, there is at the same time a pressure working on the gasket (24) (arrows 32) that ensures an increased sealing effect. This is also made clear by FIG. 4.

During injection, the plunger (12) is moved in the direction of the syringe needle, i.e. in the directions of the arrow (34).

During injection too, only a slight friction resistance occurs, since in general the gasket (24) slides along the inner wall (26), so that friction resistances between the plunger (12) and the barrel (10) in the actual sense do not have to be overcome.

Figure 5:
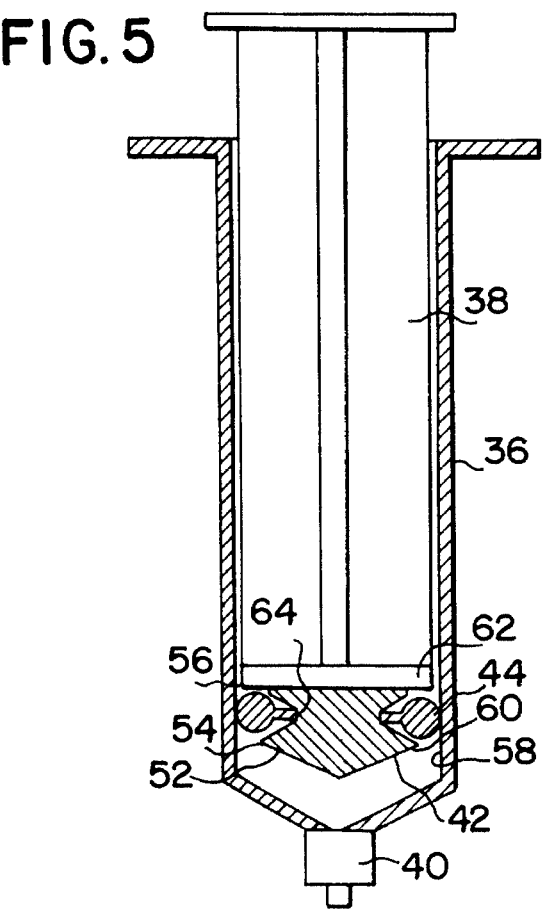
FIG. 5 shows a second embodiment of a syringe.
Figure 6:
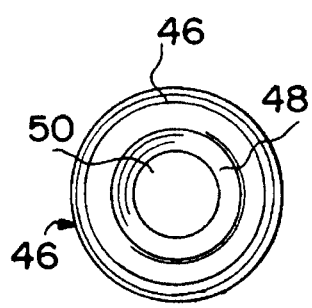
FIG. 6 shows a plan view onto a gasket.
Figure 7:
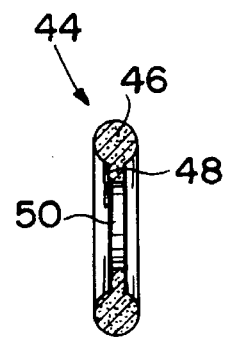
FIG. 7 shows a section through the gasket according to FIG. 6.

FIGS. 5 to 7 show a further noteworthy embodiment that is inventive per se.

As in the embodiments according to FIGS. 1 to 4, a plunger (38) is movably disposed inside a barrel (36). The barrel is shown in section from the side, in the area of its end (42) facing the syringe head (40).

The diameter of the plunger (38) is noticeably smaller than the inner diameter of the barrel (36), so that a direct contact is ruled out. Nevertheless, a secure sealing effect is achieved between the plunger (38) and the barrel (36) during both injection and sucking thanks to the teachings in accordance with the invention.

To that end, a gasket (44) is provided in the area of the front end (42) of the plunger (38) that in the actual sense comprises an O-ring (46) as the outer all-round bead and an inner section (48) having a central hole (50). The section (48) can be of membrane-like design, and can also be designed as an all-round lip extending from the outer section (46).

The correspondingly designed gasket (44), which in section has a dumbbell-like geometry with central hole, is fixed in the area (42) of the plunger (38) in a receptacle (52) formed by an all-round depression of V-shaped section.

The radially extending limits to this depression, i.e. the outer edges (54) and (56) of the receptacle (52), end at a distance from the inner wall (58) of the barrel (36).

To obtain a sealing effect, the gasket (44) has a maximum diameter equal to or greater than the inner diameter of the inner wall (58).

In the area of the salient extension (48), the limiting walls (60) and (62) of the receptacle (52) are at a distance from one another that is greater than the diameter of the section (46) of the gasket (44). Accordingly, the gasket (44) is disposed freely movable inside the receptacle (52). This freedom of movement is not in principle restricted by the membrane-like or skin-like section (48) of the gasket (44) that is in tight all-round contact with the bottom (64) of the receptacle (52) to rule out any rearward movement of the gasket (44) when the plunger (38) is at rest. The section (48) is here designed with an inherent stiffness such that resetting forces do not occur or if so only to a negligible extent, so that consequently no increased friction forces can be caused by the section (48) either.

The radial extent W of the outer section (46) of the gasket (44) is approximately double the size of the radial extent M of the inner membrane-like section (48) that tightly encloses the bottom (64) of the receptacle (52) of V-shaped section. In addition, the diameter K in the area of the bottom (64) of the plunger (38) is equal to the entire radial extent of the outer section (46) of the gasket (44), i.e. 2 W≈K.

By the design and arrangement in accordance with the invention of the gasket (44) in the embodiment shown in FIGS. 5 to 7, the same effects are obtained as in the syringe according to FIGS. 1 to 4. This means that the all-round bead (46) is in sealing contact between the limiting wall (62) and the barrel inner wall (58) during injection, and between the limiting wall (60) and the barrel inner wall (58) during sucking.

Figure 8:
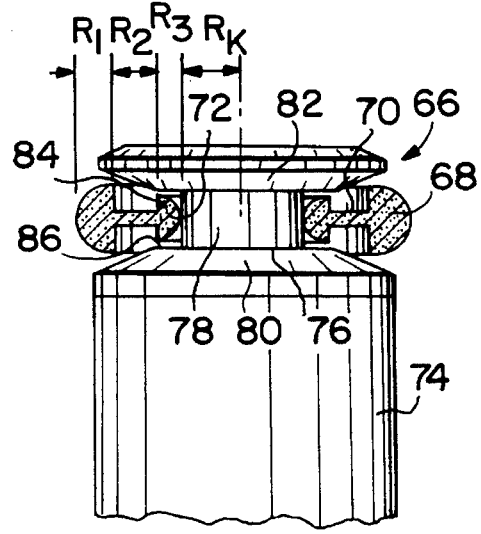
FIG. 8 shows a section of a syringe plunger with double-dumbell-shaped gasket.

FIG. 8 shows a particularly noteworthy embodiment of the invention. A gasket (66) is provided that comprises an outer semicylindrical ring (68), a web-like and annular central section (70), and an inner section (72) in the form of a semicylindrical ring. The gasket (66) tightly encloses a plunger (74) in a receptacle (76) and is at the same time in sealing contact with the inner wall of a barrel (not shown) of a syringe.

The receptacle or groove (76) has a flat bottom (78) running in the longitudinal direction of the plunger (74) and limited by walls (84) and (86) extending radially and vertically to the longitudinal axis of the plunger (74). This section of rectangular or square section adjoins an outward-tapering section that is limited by side walls (80) and (82). The opening angle between the side walls (80) and (82) should be between 30° and 50°, preferably about 40°.

In other words, the receptacle (76) is composed—when seen in section—of outer trapezoidal sections and inner square or rectangular sections.

The axial extent of the inner section of the receptacle (76) limiting it from the side walls (84) and (86) is greater than that of the inner section (72) of the gasket (66). In the radial extent too, the inner section of the receptacle (76) is greater. This means that the inner section (72) of the gasket (66) pressing against the bottom (78) with its convex side is completely inside the sectionally rectangular or square section of the receptacle (76).

The outer section (68), also equivalent to a half O-ring, and having a greater extent than the inner section (72) in both the axial and radial directions, is enclosed in some areas by the trapezoidal outer section of the receptacle (76), however with an axial extent that ensures that the section (68) of the gasket (66) is at a distance from the walls (80) and (82) when the syringe is at rest.

The gasket (66) of course protrudes with its outer section (68) radially beyond the plunger (74) in order to ensure a sealing contact with the barrel inner wall—not shown—of the syringe.

The inner section (72) has the effect of reinforcing the membrane-like or skin-like central section (70) without this causing resetting forces that hamper injection or sucking.

As a result of the fact that the inner section (72) presses against the bottom (78) of the receptacle (76) with its round outer face, a linear sealing action in relation to the bottom (78) is obtained on the one hand and a rolling motion during sucking or injection on the other hand, which does not build up a noticeable friction resistance.

The same applies in relation to the outer section (68), which also presses in approximately linear form against the barrel inner wall and performs a rolling movement along the inner face for sealing, in order to be in sealing contact with the wall (80) (injection) or the wall (82) (sucking).

Concerning the dimensions, it must be noted that the radial extent $R_1$ of the outer section (68) is approximately equal to the radial extent $R_2$ of the central section (70). To that end, the radial extent $R_3$ of the inner section (84) should be approximately half that of the central section (70) or of the outer section (68). The radius $R_K$ of the plunger in the bottom area of the receptacle (76) should by contrast be equal to or greater than the sum of the radial extents of the inner section (72) and of the central section (70).

I claim:

1. A syringe suitable for both injection and aspiration, comprising:

a) a barrel having a predetermined inner diameter;

b) a plunger movable within the barrel and having a proximal end and a distal end, said plunger comprising at the distal end, a portion of narrowed diameter disposed between two portions of greater diameter, said two portions of greater diameter being separated by a distance A; and c) a gasket disposed between said plunger and said barrel and between said two portions of greater diameter, said gasket having a diameter which is at least equal to said inner diameter and a longitudinal thickness less than or equal to said distance A, said gasket comprising an outer bead-like section contacting said barrel and said portions of said plunger, a bead-like inner portion sealing said narrowed portion of said plunger, and a central membrane-like portion connecting the outer and the inner portions, said outer and inner portions each forming a semicylindrical section and merging into each other via said central portion, said gasket being freely movable with play between said portions of said plunger when the plunger is at rest and forming a transverse seal across the inner diameter of the barrel when the plunger is in motion.

2. A syringe according to claim 1, wherein said narrowed portion comprises a v-shaped depression around the circumference of the plunger.

3. A syringe according to claim 1, wherein said narrowed portion comprises in cross section two rectangular or square inner sections and trapezoidal outer sections symmetrical to the longitudinal axis of said plunger.

4. A syringe according to claim 1, wherein the outer portion of said gasket has a radial extent that is about twice as large as the radial extent of the inner portion.

5. A syringe according to claim 1, wherein said gasket has a cross section which is double dumbbell in shape and the central portion has a radial extent that is about equal to the radial extent of the outer portion and about twice as great as the radial extent of the inner portion.

6. A syringe according to claim 1, wherein said gasket is in sealing contact between said inner wall of said barrel and a said portion of said plunger closer to said proximal end when said syringe is used for injection, and said gasket is in sealing contact between said inner wall of said barrel and said portion of said plunger closer to said distal end when said syringe is used for aspiration.

7. A syringe according to claim 1, wherein when said plunger is moved, said outer portion and said inner portion exercise a rolling movement with respect to said barrel and said portion of the plunger closer to said distal end.

\* \* \* \* \*